(12) United States Patent
Ra et al.

(10) Patent No.: US 8,455,251 B2
(45) Date of Patent: Jun. 4, 2013

(54) METHOD FOR ISOLATING AND CULTURING ADULT STEM CELLS DERIVED FROM HUMAN AMNIOTIC EPITHELIUM

(75) Inventors: Jeong Chan Ra, Gyeonggi-do (KR); Seob Il Shin, Seoul (KR); Sung Keun Kang, Seoul (KR); Sang Kyu Woo, Gyeonggi-do (KR)

(73) Assignee: RNL Bio Co., Ltd., Seoul (KR)

( * ) Notice: Subject to any disclaimer, the term of this patent is extended or adjusted under 35 U.S.C. 154(b) by 376 days.

(21) Appl. No.: 12/668,602

(22) PCT Filed: Jan. 10, 2008

(86) PCT No.: PCT/KR2008/000172
§ 371 (c)(1),
(2), (4) Date: Jun. 28, 2010

(87) PCT Pub. No.: WO2009/061024
PCT Pub. Date: May 14, 2009

(65) Prior Publication Data
US 2010/0266553 A1    Oct. 21, 2010

(30) Foreign Application Priority Data
Nov. 9, 2007 (KR) .................. 10-2007-0114451

(51) Int. Cl.
*C12N 5/00* (2006.01)
(52) U.S. Cl.
USPC ............................. 435/375; 435/325; 424/93.7
(58) Field of Classification Search
None
See application file for complete search history.

(56) References Cited

U.S. PATENT DOCUMENTS

| 2004/0235829 A1* | 11/2004 | Scott et al. | 514/227.2 |
| 2006/0234911 A1* | 10/2006 | Hoffmann et al. | 514/2 |
| 2006/0281178 A1 | 12/2006 | Sakuragawa et al. | |
| 2007/0243172 A1 | 10/2007 | Ra et al. | |

FOREIGN PATENT DOCUMENTS

| GB | 0710095 A | 6/1954 |
| WO | 2007-047468 A2 | 4/2007 |
| WO | 2007-079183 A2 | 7/2007 |
| WO | WO2007/079183 A2 | 7/2007 |

OTHER PUBLICATIONS

Lui W-Y et al. 2003. Sertoli-Germ Cell Adherens Junction Dynamics in the Testis Are Regulated by RhoB GTPase via the ROCK/LIMK Signaling Pathway. Biol. Reprod. 68: 2189-2206.*
Bain J et al. 2007. The selectivity of protein kinase inhibitors: a further update. Biochem J 408: 297-315.*
Canadian Office Action mailed Nov. 23, 2011.
Chinese Office Action mailed Sep. 26, 2011.
Supplementary European Search Report for European Application No. EP 08704712, which is counterpart to PCT/KR2008000172, dated Dec. 3, 2010.
Van der Heijden et al., "Improved procedure for the isolation of functionally active lymphoid cells from the murine intestine," Jrl. of Immunological Methods, vol. 103(2) pp. 161-167 (Nov. 5, 1987).
Jiang et al., Nature, 418:41, 2002.
Verfaillie, Trends Cell Biol., 12:502, 2002.
Toma et al., Nat. Cell Biol., 3:778, 2001.
Sampaolesi et al., Science, 301:487, 2003.
Jiang et al., Exp. Hematol., 30:896, 2002.
Miki et al., Stem Cell, 23:1549, 2005.
Watanabe et al., Nature Biotechnology, 25:681, 2007.
Wu, A. et al., 'Transplantation of human amniotic epithelial cells improves hindlimb function in rat with spinal cord injury', Chin. Med. J., 2006, vol. 119, No. 24, pp. 2101-2107.
Miki, T. et al., 'Stem cell characteristics of Amniotic Epithelial Cells', 2005, vol. 23, pp. 1549-1559.
Watanabe, K. et al., 'A ROCK inhibitor permits surviral of dissociated human embryonic stem cells.' Nature Biotech., Jun. 2007, vol. 25, No. 6, pp. 681-686.

* cited by examiner

*Primary Examiner* — Lora E Barnhart Driscoll
(74) *Attorney, Agent, or Firm* — Rabin & Berdo, P.C.

(57) ABSTRACT

The present invention relates to a method for isolating and culturing adult stem cells derived from human amniotic membrane in high yield, and more particularly to a method for obtaining a large amount of adult stem cells, the method comprising obtaining amniotic epithelial cells from human amniotic tissue in high yield by treatment with dithiothreitol (DTT) and a low concentration of trypsin and culturing the amniotic epithelial cells in a medium containing a Rho-associated kinase inhibitor. The human amniotic epithelial cell-derived stem cells are easily extracted compared to existing therapeutic stem cells such as umbilical cord blood stem cells and bone marrow stem cells, the yield and proliferation thereof are significantly increased by DTT treatment, the addition of the ROCK inhibitor or the replacement of medium. Thus, the method can be used to efficiently prepare adult stem cells.

8 Claims, 14 Drawing Sheets treating with DTT non-treating with DTT isolation

4th day from isolation
(before treating with ROCK inhibitor)

1st day after treating with
ROCK inhibitor

3rd day after treating with
ROCK inhibitor

TRA-1-60 DAPI

TRA-1-81 DAPI 0 day 1 day 3 day

Stem cells derived from amniotic epithelium of the present invention

Neurogenesis

METHOD FOR ISOLATING AND CULTURING ADULT STEM CELLS DERIVED FROM HUMAN AMNIOTIC EPITHELIUM

CROSS-REFERENCES TO RELATED APPLICATIONS

This application is a U.S. national phase application, pursuant to 35 U.S.C. §371 of PCT/KR2008/000172, filed Jan. 10, 2008, designating the United States, which claims priority to Korean Application No. 10-2007-0114451, filed Nov. 9, 2007. The entire contents of the aforementioned patent applications are incorporated herein by this reference.

TECHNICAL FIELD

The present invention relates to a method for isolating and culturing adult stem cells derived from human amniotic membrane in high yield, and more particularly to a method for obtaining a large amount of adult stem cells, the method comprising obtaining amniotic epithelial cells from human amniotic tissue in high yield by treatment with dithiothreitol (DTT) and a low concentration of trypsin and culturing the amniotic epithelial cells in a medium containing a Rho-associated kinase inhibitor.

BACKGROUND ART

Biotechnology in $21^{st}$ century presents the possibility of new solutions to food, environmental and health problems, with the ultimate object of promoting human prosperity. In recent years, the technology of using stem cells has been considered as a new way to treat incurable diseases. Previously, organ transplantation, gene therapy, etc., were presented for the treatment of incurable human diseases, but their efficient use has not been achieved due to immune rejection, short supply of organs, insufficient development of vectors, and an insufficient knowledge of disease genes.

For this reason, with increasing interests in stem cell studies, it has been recognized that totipotent stem cells having the ability to form all the organs by proliferation and differentiation can not only treat most of diseases but also fundamentally heal organ injuries. Also, many scientists have suggested clinical applicability of stem cells for the regeneration of all the organs and the treatment of incurable diseases, including Parkinson's disease, various cancers, diabetes and spinal damages.

Stem cells refers to cells having not only self-replicating ability but also the ability to differentiate into at least two cells, and can be divided into totipotent stem cells, pluripotent stem cells, and multipotent stem cells.

Totipotent stem cells are cells having totipotent properties capable of developing into one perfect individual, and these properties are possessed by cells up to the 8-cell stage after the fertilization of an oocyte and a sperm. When these cells are isolated and transplanted into the uterus, they can develop into one perfect individual.

Pluripotent stem cells, which are cells capable of developing into various cells and tissues derived from the ectodermal, mesodermal and endodermal layers, are derived from an inner cell mass located inside of blastocysts generated 4-5 days after fertilization. These cells are called "embryonic stem cells" and can differentiate into various other tissue cells but not form new living organisms.

Multipotent stem cells, which are stem cells capable of differentiating into only cells specific to tissues and organs containing these cells, are involved not only in the growth and development of various tissues and organs in the fetal, neonatal and adult periods but also in the maintenance of homeostasis of adult tissue and the function of inducing regeneration upon tissue damage. Tissue-specific multipotent cells are collectively called "adult stem cells".

Adult stem cells are obtained by taking cells from various human organs and developing the cells into stem cells and are characterized in that they differentiate into only specific tissues. However, recently, experiments for differentiating adult stem cells into various tissues, including liver cells, succeeded and thus are receiving attention.

The multipotent stem cells were first isolated from adult bone marrow (Jiang et al., *Nature*, 418:41, 2002), and then also found in other various adult tissues (Verfaillie, *Trends Cell Biol.*, 12:502, 2002). In other words, although bone marrow is the most widely known source of stem cells, the multipotent stem cells were also found in the skin, blood vessels, muscles and brains (Tomas et al., *Nat. Cell Biol.*, 3:778, 2001; Sampaolesi et al., *Science*, 301:487, 2003; Jiang et al., *Exp. Hematol.*, 30:896, 2002). However, stem cells are very rarely present in adult tissues, such as bone marrow, and such cells are difficult to culture without inducing differentiation, and thus difficult to culture in the absence of specifically screened media. Namely, it is very difficult to maintain the isolated stem cells in vitro.

Meanwhile, the results of studies on the isolation of mesenchymal stem cells from fetal tissue revealed that there are abundant mesenchymal stem cells in fetal tissue. However, the use of fetal tissue as a source of cell therapeutic agents has been limited due to ethical concerns. Mesenchymal stem cells were also isolated from umbilical cord blood (UCB) as the source of fetal mesenchymal stem cells (MSCs), but their numbers were very small, and they show poor proliferation.

On the other hand, in the case of placenta stem cells which are receiving a great deal of attention recently due to excellent differentiation potential and safety, mesenchymal stem cells can be extracted in an amount 100 times larger than that of those from umbilical cord blood. Moreover, umbilical cord blood can be used only once, and donor umbilical cord blood is additionally needed after the age of 15 years, whereas placenta stem cells can be used several times, and thus can also be used in adults. In addition, placenta stem cells can be used for a wider range of diseases. Hematopoietic stem cells of umbilical cord blood are mainly used for blood diseases, whereas placenta stem cells can be advantageously used for treating cellular injury and can be used in the future for treating many diseases, including heart failure, stroke, diabetes, osteoporosis, degenerative arthritis and the like.

However, in the case of using the placenta as the source of adult stem cells, is difficult to use placenta tissue collected immediately after delivery, whenever needed, and in fact, for the industrial application (placenta injection, placenta cosmetic products, etc.) of placenta tissue, placenta tissue collected after delivery is cold stored for use. Placenta-derived stem cells present in an undifferentiated state can be obtained in a large amount only from the placenta collected immediately after delivery, and it is very difficult to obtain a large amount of adult stem cells from placenta tissue several hours after delivery or particularly from placenta tissue that has been cold-stored for a long period of time.

For this reason, in order to use placenta-derived adult stem cells in industrial applications there is an urgent need to develop technologies for preparing a large amount of adult stem cells from cold-stored placenta tissue or the like. Among adult stem cells, it is known that adult stem cells derived from amniotic epithelial cells possess properties most similar to the properties of embryonic stem cells, and thus have the capability to differentiate into various cells, while they are clinically safe, because they do not cause cancer upon in vivo transplantation, unlike embryonic stem cells (Miki et al., *Stem Cell*, 23:1549, 2005). The adult stem cells derived from amniotic epithelial cells are more likely to proceed to apoptosis during the culture and subculture of single cells, unlike adult stem cells derived from other placenta tissues. For this reason, it is difficult to induce proliferation of undifferentiated adult stem cells derived from amniotic epithelial cells in large numbers using conventional culture methods (http://www.cellapplications.com/HumanCells/HPlEpC.htm).

Accordingly, the present inventors have made many efforts to prepare a large amount of undifferentiated adult stem cells derived from amniotic epithelial cells for practical applications thereof and, as a result, have found that a large amount of stem cells derived from amniotic epithelial cells can be obtained from cold-stored placenta tissue by using DTT and a ROCK inhibitor to isolate and culture amniotic epithelial cells and changing the composition of culture medium, thereby completing the present invention.

SUMMARY OF INVENTION

It is an object of the present invention to provide a method for isolating amniotic epithelial cells from human amniotic tissue with high yield and a method for preparing adult stem cells derived from the isolated amniotic epithelial cells.

Another object of the present invention is to provide adult stem cells derived from human amniotic epithelial cells and a cell therapeutic agent for wound healing, which contains the adult stem cells as an active ingredient.

To achieve the above objects, the present invention provides a method for isolating amniotic epithelial cells, comprising the steps of: treating human amniotic tissue with dithiothreitol (DTT); and treating the DTT-treated human amniotic tissue with 0.025-0.125% trypsin.

The present invention also provides a method for preparing adult stem cells derived from human amniotic epithelial cells, the method comprising the steps of: culturing human amniotic epithelial cells isolated according to said method in a medium containing a Rho-associated kinase (ROCK) inhibitor; and collecting stem cells from the culture broth.

The present invention also provides a method for proliferating and maintaining adult stem cells derived from human amniotic epithelial cells, the method comprising subculturing human amniotic epithelial cell-derived adult stem cells prepared according to said method in a medium containing a Rho-associated kinase (ROCK) inhibitor.

The present invention also provides human amniotic epithelial tissue-derived adult stem cells prepared by said method and a cell therapeutic agent for wound healing, which contains the adult stem cells as an active ingredient.

Other features and embodiments of the present invention will be more apparent from the following detailed description and the appended claims.

DETAILED DESCRIPTION OF THE INVENTION AND PREFERRED EMBODIMENTS

Figure 1:
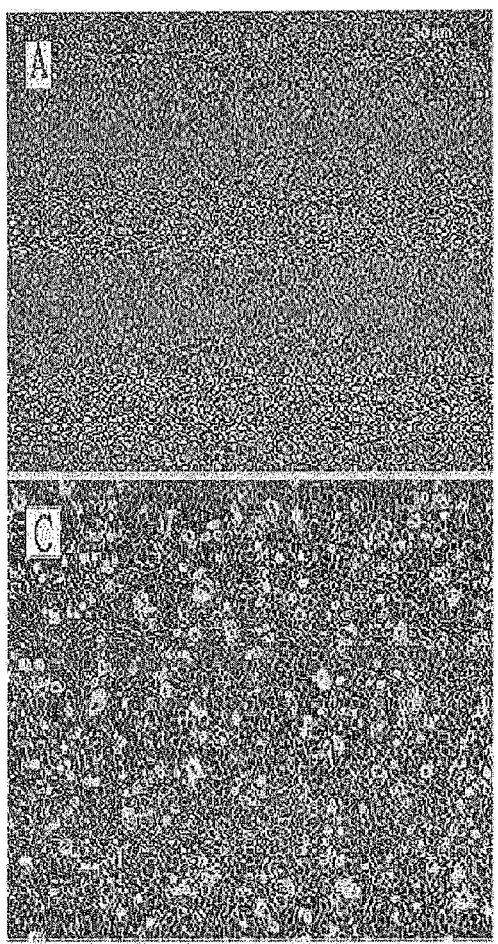
FIG. 1 shows a comparison between the yields of amniotic epithelial cells after treatment with or without dithiothreitol (DTT) [A: amniotic epithelial cells obtained by treatment with DTT and trypsin; B: single cells obtained by treatment with trypsin alone; C: adult stem cells obtained by culturing "A"; and D: adult stem cells obtained by culturing "B"].
Figure 1:
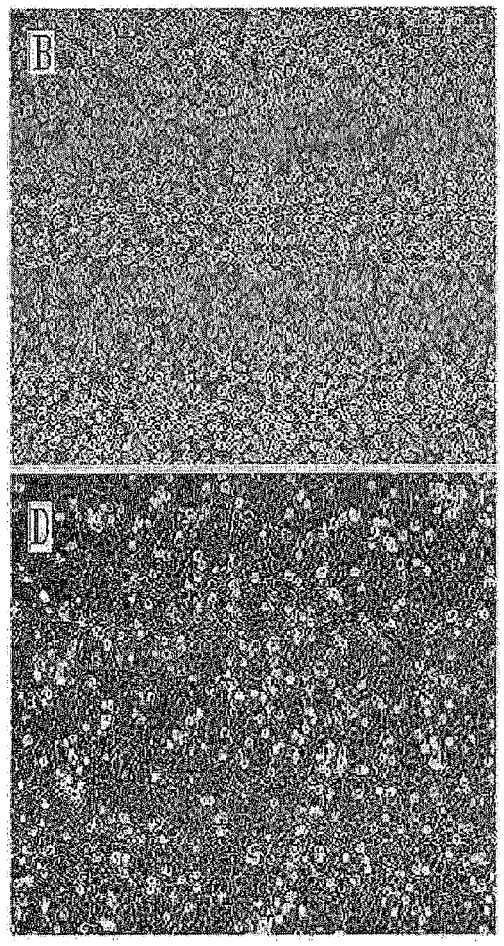

In one aspect, the present invention relates to a method for isolating and preparing amniotic epithelial cells with high yield, the method comprising the steps of: treating human amniotic tissue with dithiothreitol (DTT); and treating the DTT-treated human amniotic tissue with a low concentration of trypsin.

The present invention is characterized in that, rather than extracting various kinds of cells from amniotic tissue isolated from the placenta, only amniotic epithelial cells are extracted and isolated from the amniotic tissue. Amniotic epithelial cells develop from the epiblast by 8 days after fertilization and before gastrulation, and they maintain the plasticity of pregastrulation embryo cells.

Thus, it was found that the amniotic epithelial cells express the same surface markers as those on embryonic stem cells. The results of immunohistochemical and genetic analysis revealed that adult stem cells derived from amniotic epithelial cells have the ability to differentiate into endoderm-derived, mesoderm-derived and ectoderm-derived cells and do not cause tumor formation in vivo (Miki et al., *Stem Cell*, 23:1549, 2005).

However, adult stem cells derived from amniotic epithelial cells are more likely to proceed to apoptosis during the culture and subculture of single cells, unlike adult stem cells derived from other placenta tissues, and for this reason, it is difficult to induce proliferation of undifferentiated adult stem cells derived from amniotic epithelial cells in large numbers using conventional culture methods. In other words, amniotic epithelial cell-derived stem cells present in an undifferentiated state can be obtained in a large amount only from the placenta collected immediately after delivery, and it is very difficult to obtain a large amount of adult stem cells from placenta tissue several hours after delivery or particularly from placenta tissue that has been cold-stored for a long period of time. Due to such a problem, it is necessary to obtain a large amount of amniotic epithelial cells from the placenta harvested immediately after delivery or inhibit apoptosis of adult stem cells during cell culture.

The surface of amniotic membrane isolated from the placenta is usually covered with blood and mucus. Such mucus and the like interfere isolation of single cells from amniotic membrane and function to reduce the effect of trypsin treatment in the prior art. Thus, it is required to remove impurities such as mucus before trypsin treatment, and thus create an environment in which the effect of trypsin used for the isolation of single cells can be maximized.

The present invention relates to a method for obtaining a large amount of amniotic epithelial cells from the placenta harvested immediately after delivery by treating with dithiothreitol (DTT) before trypsin treatment and culturing the isolated cells in a large amount by inhibiting apoptosis of the isolated cells, and thus solves the above-described problem.

DTT is a compound represented by the following structural formula 1, which is generally used for the removal of disulfide bonds from proteins, inhibition of dimmer formation in DNA, the removal of mucus, the removal of debris or connective tissue, and the like, and it is a reagent added to many biological test compositions, but has not been used in a process of extracting stem cells.

[Structural Formula 1]

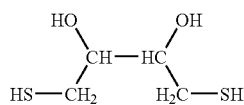

In the present invention, excessive cell disruption is prevented by substituting trypsin treatment, which is a conventional procedure for isolating single cells, with DTT treatment, and the yield of single cells is increased by removing mucus that interferes with the effect of trypsin treatment to be performed later.

Herein, the concentration of DTT used for the treatment is preferably 5-50 mM, and more preferably 8-15 mM. In one embodiment of the present invention, 10 mM of DTT was used. If DTT is used at a concentration of less than 5 mM, it is difficult to obtain single cells with high yield, and if DTT is used at a concentration of more than 50 mM, apoptosis may occur due to excessive protein degradation.

After human amniotic tissue is treated with DTT, it is treated with a low concentration of trypsin in order to isolate amniotic epithelial cells. The concentration of trypsin is preferably 0.025-0.125%, and more preferably 0.05-0.10%.

In order to isolate various kinds of cells from amniotic tissue, treatment with trypsin at suitable concentrations corresponding thereto is required, and particularly, amniotic epithelial cells are obtained by treatment with a low concentration of trypsin. However, in the prior art, epithelial cells could not be effectively isolated with a low concentration of trypsin due to the interference caused by impurities such as mucus covering amniotic tissue, and for this reason, mesenchymal stem cells (MSCs) that can be isolated with a high concentration of trypsin or collagenase have been used generally.

However, the present invention enables amniotic epithelial cells to be effectively isolated even with a low concentration of trypsin by removing mucus and the like though treatment of human amniotic tissue with DTT. Specifically, the present invention provides a method of isolating amniotic epithelial cells in high yield by treatment with a low concentration (0.025-0.125%) of trypsin, not treatment with a high concentration (0.25-0.5%) of trypsin.

Herein, the yield of cells can be increased by applying a physical shear stress though an additional step of vortexing at 2500-3000 rpm for 30-60 seconds immediately after trypsin treatment. This additional process has an advantage in that it relatively shortens the trypsin treatment time and thus reduces cell damage caused by trypsin.

After amniotic tissue is subjected to trypsin treatment and vortexing, the resulting material is filtered, thus obtaining desired amniotic epithelial cells. Preferably, the resulting material is primarily filtered through a 1-2 mm mesh, and as a result, the in vitro exposure time of cells can be reduced compared to the case in which a 100-μm strainer is used from the beginning, thus increasing the viability of cells, reducing the time taken for cell isolation, and reducing the use of the 100-μm cell strainer, which leads to cost reduction.

When amniotic epithelial cells isolated according to the above method are cultured in a medium containing a Rho-associated kinase (ROCK) inhibitor, a large amount of adult stem cells can be obtained.

Therefore, the present invention, in another aspect, relates to a method for preparing adult stem cells derived from human amniotic epithelial cells, the method comprising the steps of: culturing human amniotic epithelial cells isolated according to said method in a medium containing a Rho-associated kinase (ROCK) inhibitor; and collecting adult stem cells from the culture broth. Furthermore, the present invention relates to a method for proliferating and maintaining adult stem cells derived from human amniotic epithelial cells, the method comprising subculturing human amniotic epithelial cell-derived adult stem cells prepared according to said method in a medium containing a Rho-associated kinase (ROCK) inhibitor.

A medium which is used in the culture of amniotic epithelial cell-derived adult stem cells in the present invention may be a conventional medium such as DMEM (dulbecco modified eagle medium) or K-SFM (keratinocyte serum free medium). The medium may contain ascorbic acid, epidermal growth factor (EGF), insulin, antibiotics, FBS (fetal bovine serum), etc. The antibiotics may be conventional antibiotics known in the art, and an example thereof may be antibiotic-antimycotic (Gibco).

Figure 7:
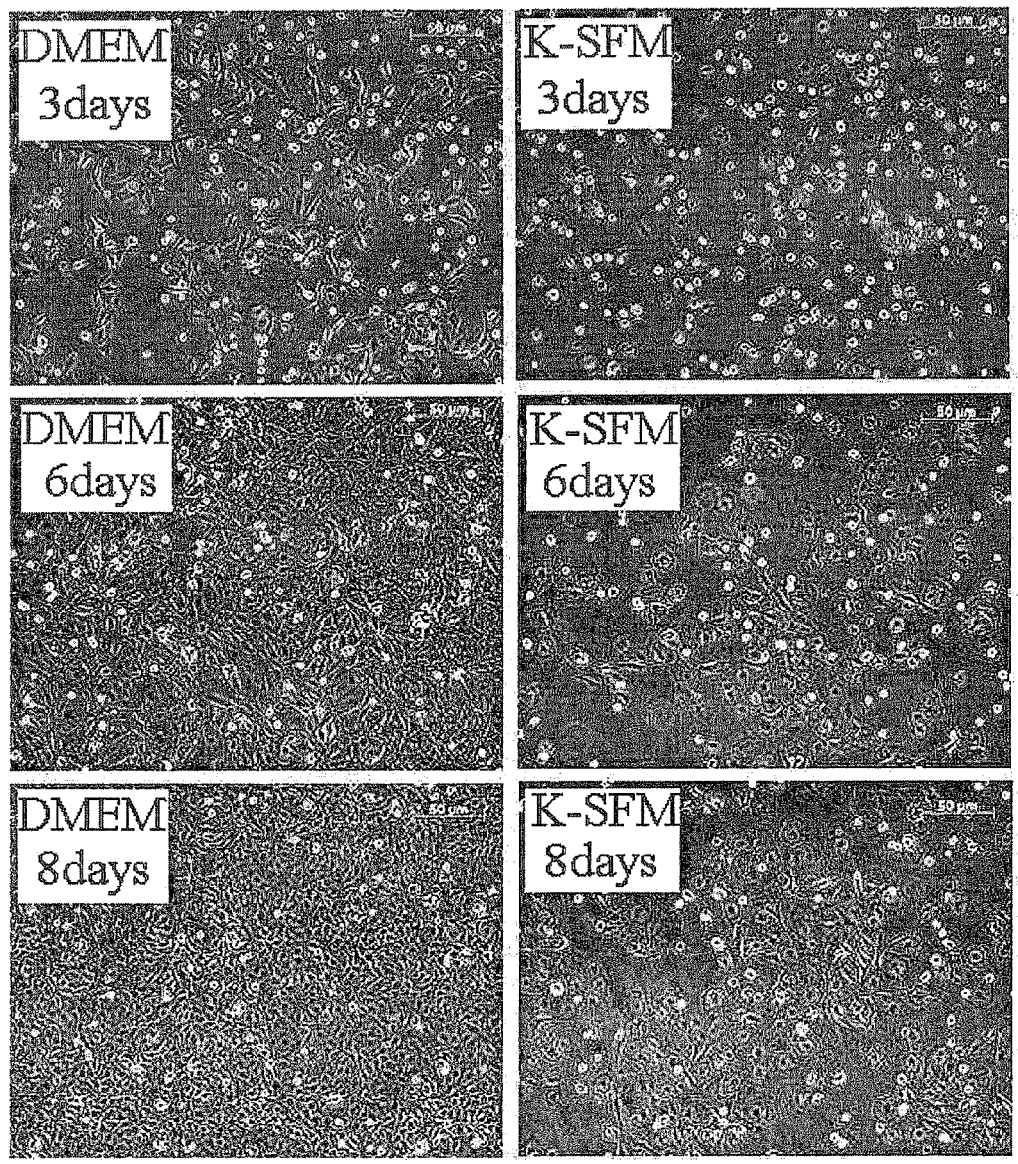
FIG. 7 shows the results obtained by comparing the ability of amniotic epithelial cell-derived adult stem cells to proliferate by culturing them in each of DMEM medium and K-SFM medium for 3 days, 6 days and 8 days, respectively.

As the culture medium, for example, a DMEM (dulbecco modified eagle medium) containing FBS (fetal bovine serum), ascorbic acid, epidermal growth factor, nonessential amino acids and antibiotics, or a K-SFM (keratinocyte serum free medium) containing FBS, ascorbic acid, hydrocortisone, NAC(N-acetyl-L-cysteine), insulin and antibiotics may be used to culture amniotic epithelial stem cells. Herein, the proliferation of adult stem cells was shown to be somewhat higher when cultured in the DMEM medium than that when cultured in the K-SFM medium (FIG. 7).

Figure 8:
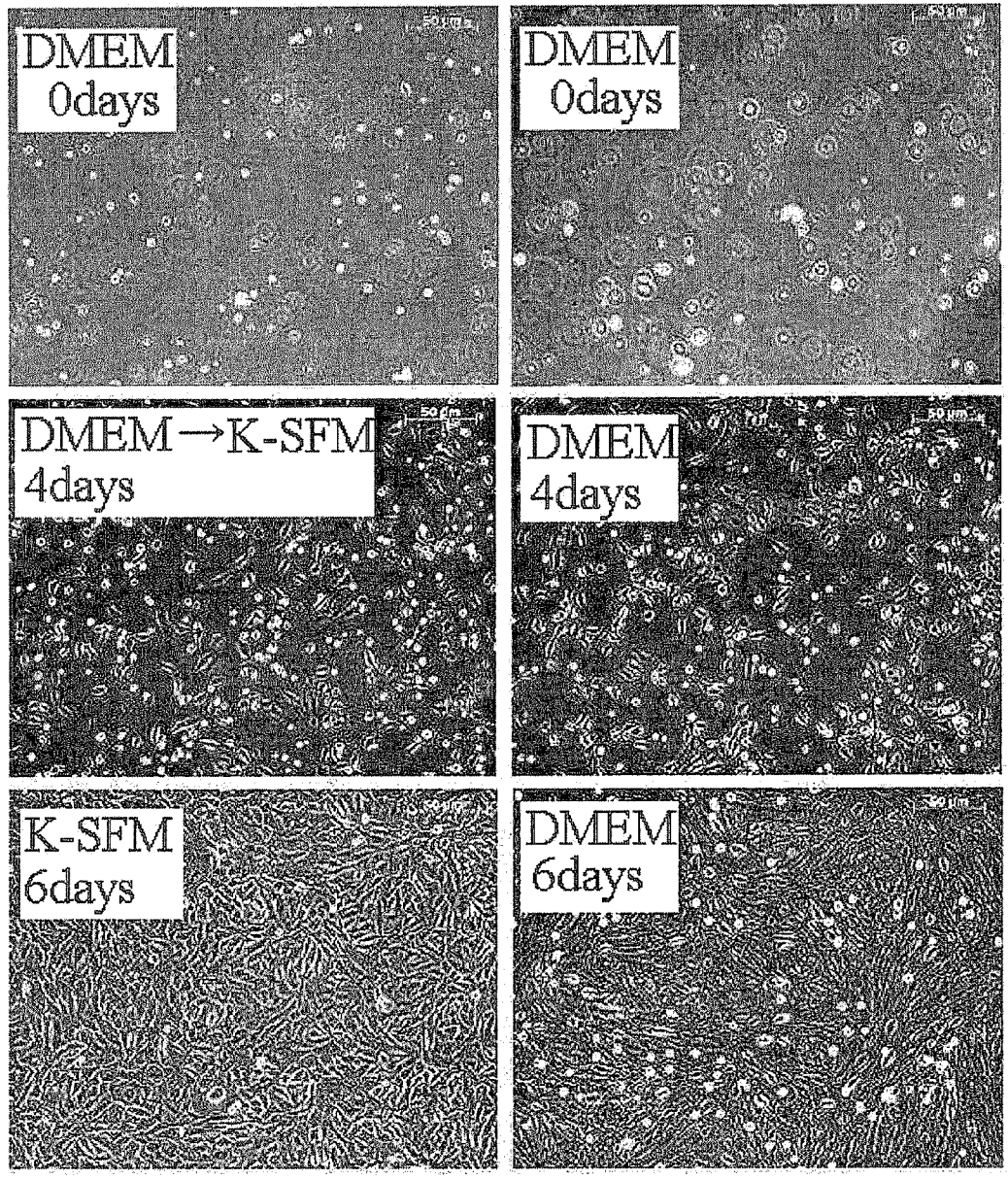
FIG. 8 shows a comparison of enhanced ability of amniotic epithelial cell-derived adult stem cells to proliferate by the replacement of DMEM medium and K-SFM medium.

Particularly with respect to the media, the present inventors examined the ability of cells to proliferate through the experiment performed by replacement of the DMEM and K-SFM media and, as a result, found that, when the DMEM medium was replaced with the K-SFM, the ability of adult stem cells to proliferate was further increased compared to when only the DMEM or K-SFM medium was continuously used (not replaced) (FIG. 8). In this process, the replacement of the DMEM medium with the K-SFM medium is preferably performed in the primary subculture of adult stem cells.

However, the culture medium for amniotic epithelial cell-derived adult stem cells is most preferably a mixed medium (Gibco) consisting of a 1:1 mixture of DMEM and F-12 (nutrient mixture). At this time, the mixed medium may also contain ascorbic acid, epidermal growth factor (EGF), insulin, antibiotics and FBS (fetal bovine serum). In one embodiment of the present invention, antimycotic-antibiotics (Gibco) were used as antibiotics.

In the present invention, isolated single amniotic epithelial cells were primarily cultured in a medium containing a ROCK (Rho-associasted kinase) inhibitor to obtain adult stem cells, and then subcultured in the presence of the ROCK inhibitor, such that the adult stem cells are maintained in an undifferentiated state.

The ROCK (Rho-associated kinase) inhibitor, which is a substance functioning to inhibit apoptosis, is known to inhibit agonist-induced $Ca^{2+}$ sensitization of neurite regeneration, myosin phosphorylation and smooth muscle contraction. More specifically, the ROCK inhibitor is known to normalize the abnormal structure of muscle cells that causes hypertension and asthma and to have the function of increasing blood flow to the optic disc and continuously reducing intraocular pressure. With respect to biological properties, the ROCK inhibitor is known to have the function of inhibiting apoptosis and maintaining cells in an undifferentiated state. Recently, studies on the use of the ROCK inhibitor to increase the viability of isolated human embryonic stem cells were conducted (Watanabe et al., *Nature Biotechnology*, 25:681, 2007).

However, it is obvious to those skilled in the art that embryonic stem cells and adult stem cells are clearly distinguished from each other thus the sources and differentiation abilities thereof clearly differ from each other. There has been no report confirming that proliferation of adult stem cells is increased by using a ROCK inhibitor. However, in the present invention, it was confirmed that the ability of adult stem cells to proliferate was increased by a ROCK inhibitor in the isolation and culture thereof, and also the efficiency of proliferating and maintaining amniotic epithelial cell-derived stem cells was further increased by the ROCK inhibitor.

In the above study conducted by Watanabe et al., a method of treating embryonic stem cells with a ROCK inhibitor before reseeding the cells into a fresh medium for subculture was used. Specifically, after the embryonic stem cells treated with the ROCK inhibitor were reseeded on a fresh medium, they were cultured without treatment with the ROCK inhibitor (Watanabe et al., *Nature Biotechnology*, 25:681, 2007).

On the other hand, in the present invention, a ROCK inhibitor was treated to the cells as reseeding on a fresh medium for subculture, thus establishing an environment in which the ROCK inhibitor was continuously present during the subculture of human amniotic epithelial cell-derived stem cells.

Typical ROCK inhibitors that can be used in the present invention include Y-27632, HA-1077, Y-39983, Wf-536, etc., and among them, Y-27632 (Calbiochem or Sigma) was used in exemplary embodiments of the present invention. Y-27632 has the following structural formula 2:

[Structural formula 2]

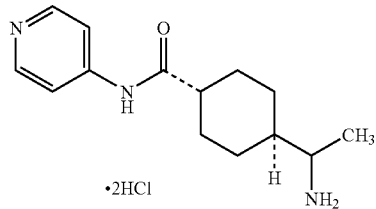

The concentration of the ROCK inhibitor which is used in treatment according to the present invention is preferably in the range from 10 nM to 100 μM. If the ROCK inhibitor is used at a concentration of less than 10 nM, it will be difficult to maintain an undifferentiated state adult stem cells for a long period of time, and if the ROCK inhibitor is used at a concentration of more than 100 μM, a cell morphology change may occur, and cells may enter into the differentiation process.

In another aspect, the present invention relates to amniotic epithelial cell-derived adult stem cells, obtained by the method as described above. The morphological and immunological characteristics of amniotic epithelial cell-derived adult stem cells, obtained by the method as described above will now be described as follows.

(1) Morphological Characteristics

Figure 12:
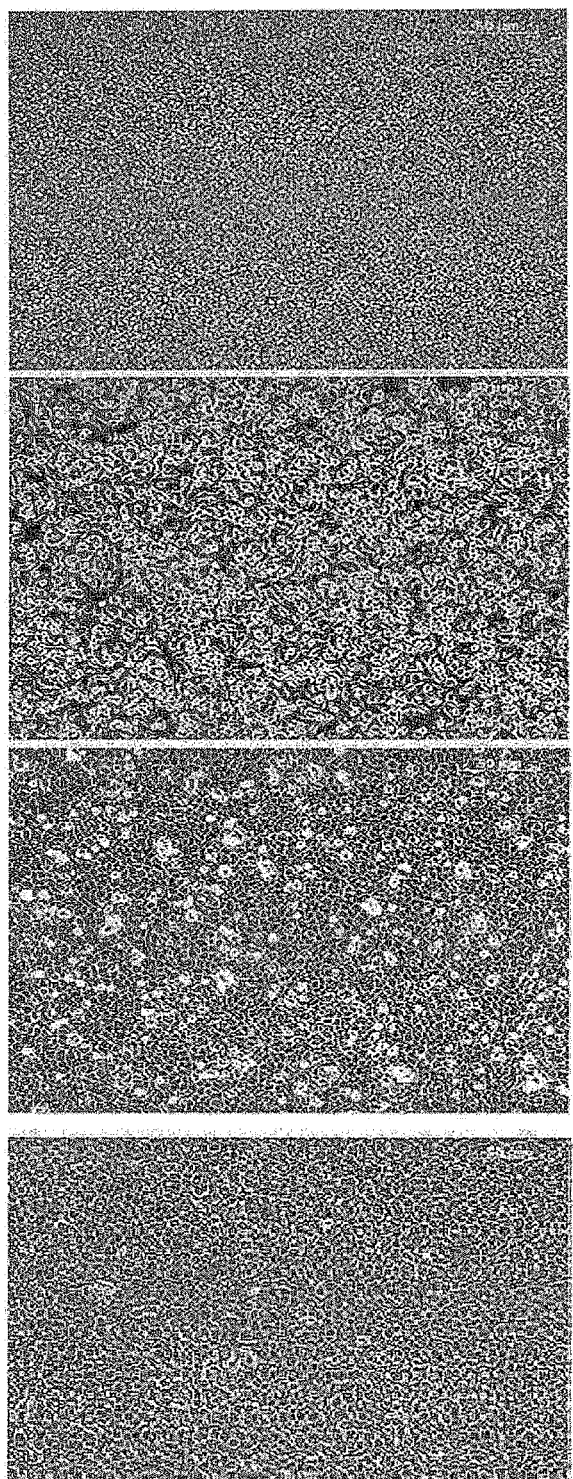
FIG. 12 is optical microscope photographs showing the morphological characteristics of amniotic epithelial cell-derived adult stem cells.

Single amniotic epithelial cells isolated from amniotic tissue have the typical morphology of rectangular parallelepiped- or dice-shaped, slightly rounded epithelial cells, and the size of the cells during the culture is about 5-10 μm. Generally, amniotic epithelial cells increase in size depending on culture conditions, while the cytosol is increased, which causes trophoblastic change, or they are likely to undergo deformations associated with epithelio-mesenchymal transition by which epithelial cells undergo dramatic morphology changes into mesenchymal stem cell (MSC) type (FIG. 12). However, in the present invention, amniotic epithelial cell-derived adult stem cells treated with DTT and cultured in a ROCK inhibitor-containing medium continuously maintain a simple cuboidal shape (the bottommost photograph of FIG. 12).

(2) Immunological Characteristics

Figure 9:
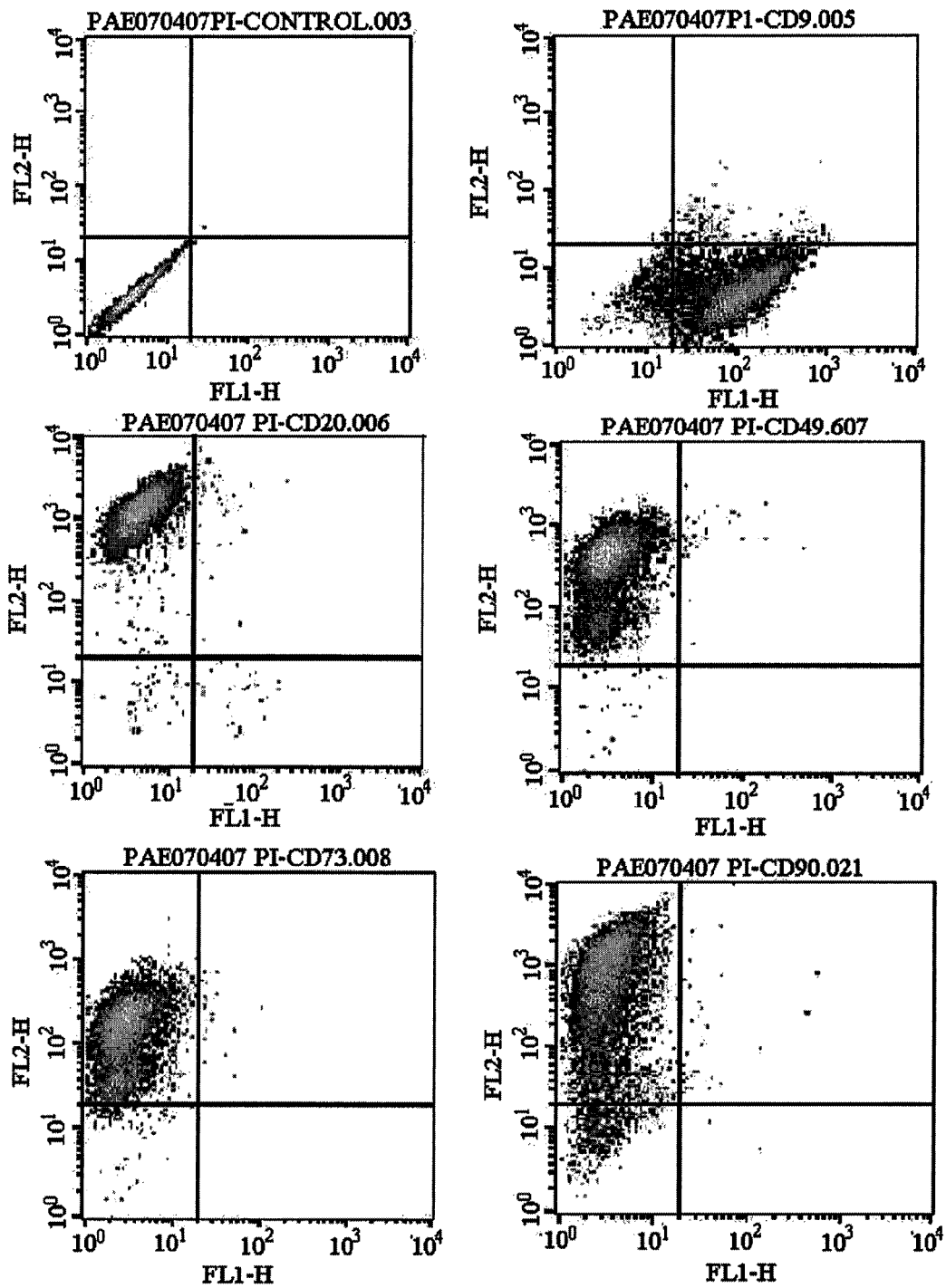
FIGS. 9 and 10 show the results of flow cytometric analysis of amniotic epithelial cell-derived adult stem cells.
Figure 10:
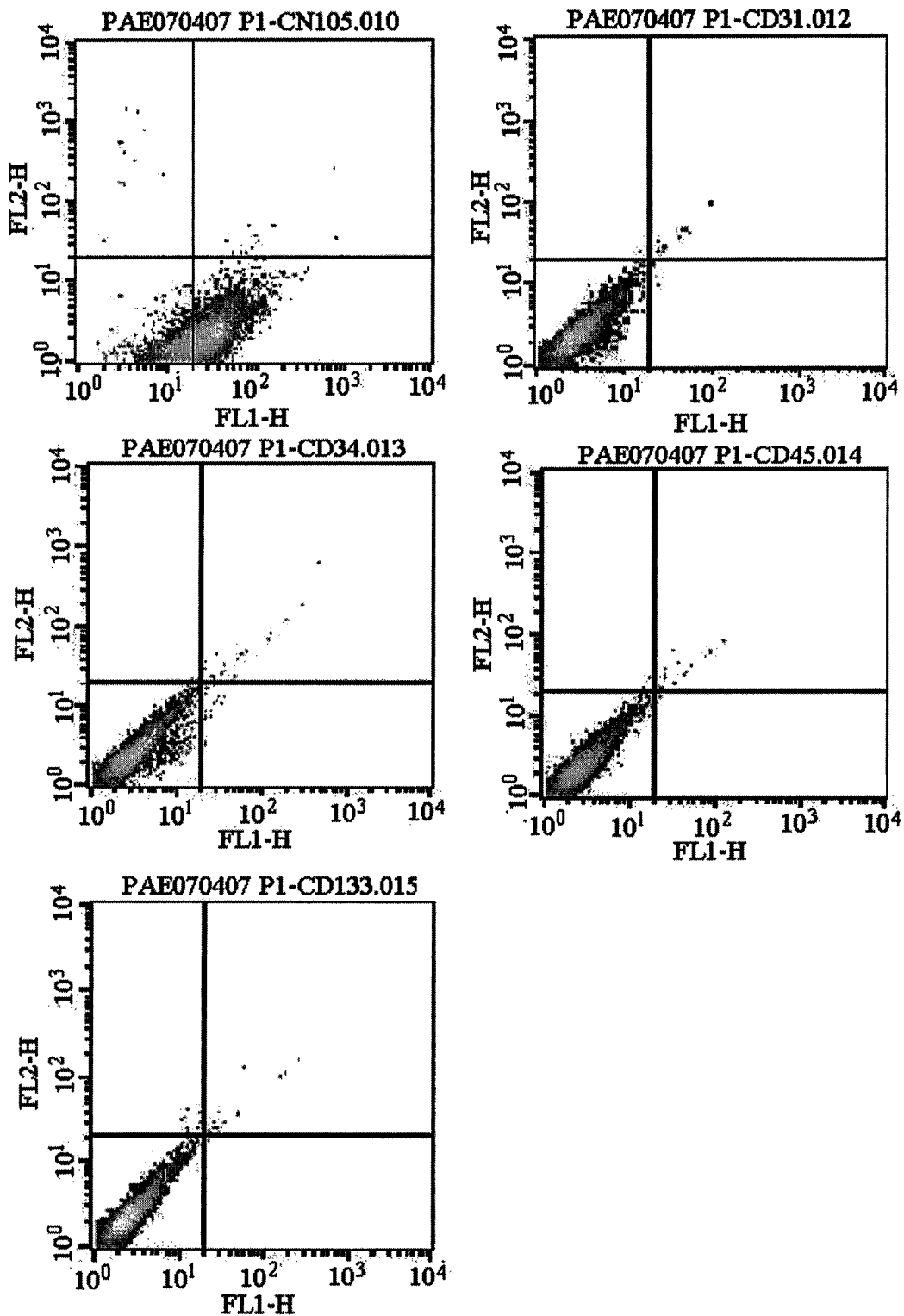

Immunological characteristics of amniotic epithelial cell-derived adult stem cells according to the present invention were analyzed using a flow cytometer and, as a result, cells were positive for CD9, CD29, CD49f, CD73, CD90 and CD105, and negative for CD31, CD34, CD45 and CD133 (FIGS. 9 and 10).

(3) Sternness

Figure 11:
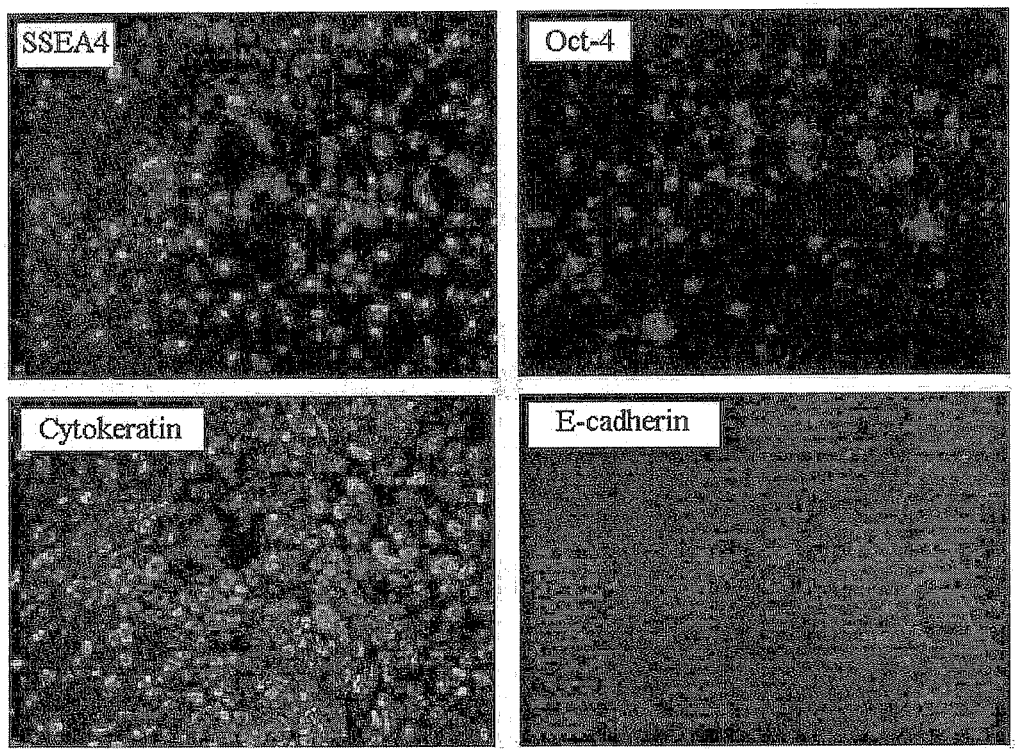
FIG. 11 is photographs showing the responses of amniotic epithelial cell-derived adult stem cells to SSEA4, Oct-4, Cytokeratin and E-cadherin.
Figure 11:
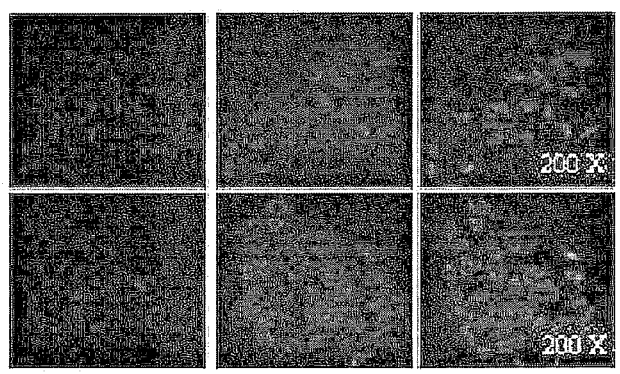

It was found that, in the amniotic epithelial cell-derived adult stem cells of the present invention, cytokeratin and epithelium (E)-cadherin which indicate the characteristics of epithelial cells were expressed, and SSEA 4, Oct-4, Tra-1-60 and Tra-1-81 which are known as markers of totipotent stem cells were also expressed (FIG. 11).

Moreover, with respect to the differentiation ability of stem cells, amniotic epithelial cells have characteristics most similar to those of embryonic stem cells as already known in the art, and thus the inventive adult stem cells derived from the amniotic epithelial cells also have differentiation ability similar to that of embryonic stem cells, that is, the ability to differentiate into endoderm-, mesoderm- and ectoderm-derived cells. In the present Example 6, the ability of the inventive adult stem cells to differentiate into mesoderm-derived adipocytes, osteoblasts and myocytes and ectoderm-derived neurocytes, was confirmed.

In still another aspect, the present invention relates to a cell therapeutic agent for treating wounds in the body and on the surface of the body, which contains adult stem cells as an active ingredient.

As used herein, the term "wound" means a bodily injury caused by physical means which resulted in disruption of the continuity of structures and is meant to include destruction, cutting or rupture, etc. of the skin, mucosa or bone tissue.

The inventive cell therapeutic agent for treating wounds, which contains adult stem cells as an active ingredient, can be administered directly to the diseased site in addition to parenteral administration in the form of intravenous or intramuscular injections. The cell therapeutic agent of the present invention may be administered by various routes, including transdermal, subcutaneous, intravenous and intramuscular routes.

Formulations for parenteral administration include sterile aqueous or non-aqueous solutions, suspensions, emulsions, etc. For the non-aqueous solution and suspension, propylene glycol, polyethylene glycol, vegetable oil such as olive oil, injectable esters such as ethyloleate or the like may be used.

For humans, the cell therapeutic agent may be administered, generally at a dose of $10^4$-$10^{10}$ cells/body, and preferably $10^6$-$10^8$ cells/body, once or several times a day.

However, it is to be understood that the actual dose of the active ingredients should be determined by various related factors such as administration route disease to be treated, patient's age, sex and weight, and the severity of disease. Thus, the above-mentioned dose ranges of the active ingredients do not limit the scope of the present invention in any way.

The adult stem cells of the present invention can be advantageously used for tissue repair and wound healing. The inventive amniotic epithelial cell-derived adult stem cells possessing characteristics similar to those of embryonic stem cells have the ability to differentiate into endodermal, mesodermal and ectodermal cells, and thus can be used for wound healing and tissue repair and regeneration. In addition, the adult stem cells can differentiate, and proliferate and regenerate into bone, cartilage, muscle, ligament and/or nerve tissues, and thus are useful as a cell therapeutic agent.

EXAMPLES

Hereinafter, the present invention will be described in further detail with reference to examples. It is to be understood, however, that these examples are for illustrative purposes only and are not to be construed to limit the scope of the present invention.

Various media and reagents used in the following examples were purchased from the companies shown in Table 1 below.

TABLE 1

| | Items | Brand | Catalogue No. |
|---|---|---|---|
| Media | DMEM/F-12 | Gibco | 11320 |
| | EGF | Sigma | E 9644 |
| | | Peprotech | 100-15 |
| | | Gibco | 13247-051 |
| | FBS | Gibco | 16000 |
| | Insulin | Sigma | I 1882 |
| | Ascorbic acid | Sigma | A 8960 |

TABLE 1-continued

| | Items | Brand | Catalogue No. |
|---|---|---|---|
| | Antibiotic-antimycotic | Gibco | 15240 |
| ROCK inhibitor | Y-27632 | Calbiochem | CNB 688000 |
| | | Sigma | Y 0503 |
| Trypsin solution | Trypsin-EDTA | Gibco | 15400 |
| | L/G DMEM | Gibco | 11885 |
| Buffer solution | HBSS | Gibco | 14175 |
| Subculture | TrypLE-Express | Gibco | 12604 |
| DTT | DTT | Gibco | 15508-013 |

Example 1

Isolation of Amniotic Epithelial Cells from Amniotic Tissue by Treatment with DTT (Dithiothreitol) and Trypsin Amniotic membranes were collected at normal births and premature births in Korea University Guro Hospital according to the Institutional Review Board Guidelines of Korea University and used for research purposes. Amniotic tissue required in experiments was isolated from the placenta, and the isolated tissue was stored in an antibiotic-containing physiological saline or DMEM medium.

5 g of amniotic tissue was weighed and washed with HBSS. For stable isolation of amniotic epithelial cells, the washing process was carried out using HBSS buffer more similar to the constituents of the human body rather than using general PBS. The washed amniotic tissue was transferred into a 50-ml tube, and 10 mM DTT was added thereto. After treatment with DTT for 30 minutes, the supernatant was discarded, the amniotic tissue was finely cut, and the finely cut amniotic tissue was treated with fresh 0.05% trypsin-EDTA at 37° C. for 42 minutes under stirring, thus chemically degrading the tissue. The chemically degraded tissue was vortexed for 1 minute, and then it was primarily filtered through a 1-mm mesh and secondarily filtered through a 100-μm mesh, thus removing non-degraded tissue. The filtered tissue was centrifuged at 1800 rpm for 10 minutes. The single cell pellets at the bottom were well suspended, thus obtaining amniotic epithelial cells.

Living cells were visually counted under a microscope using a hemocytometer according to trypan blue dye method and, as a result, the number of cells counted immediately after isolation was $3.72 \times 10^7$ cells (FIG. 1 (A)).

On the other hand, in the case in which amniotic epithelial cells were isolated from amniotic tissue by treatment with trypsin alone without the addition of DTT, the number of cells counted immediately after isolation was $9.25 \times 10^5$ cells (FIG. 1 (B)).

As a result, as shown in FIG. 1, the number of amniotic epithelial cells isolated by treatment with DTT (A) and trypsin and the number of cells after the culture of the amniotic epithelial cells (C) were significantly larger than the number of amniotic epithelial cells isolated by treatment with trypsin alone without DTT treatment (B) and the number of cells after the culture thereof (D). From this, it was found that, when amniotic tissue was treated with DTT, excessive cell disruption could be inhibited and, in addition, mucus interfering with the effect of trypsin treatment to be treated thereafter could be removed, thus further increasing the yield of amniotic epithelial cells. Furthermore, it was confirmed that, as the initial yield of amniotic epithelial cells was increased, the amount of adult stem cells which could be obtained by culturing the amniotic epithelial cells was also significantly increased.

Example 2

Culture of Amniotic Epithelial Cells in the Presence of ROCK Inhibitor 2-1: Culture of Amniotic Epithelial Cells The obtained amniotic epithelial cells were cultured in a medium (Gibco) consisting of a 1:1 mixture of DMEM (Dulbecco modified Eagle medium) and F-12 (nutrient mixture) to which FBS, ascorbic acid, epidermal growth factor, insulin, an antibiotic and 10 µM of ROCK inhibitor Y-27632 have been added at the concentrations shown in Table 2 below.

TABLE 2

| Component | Concentration | Component | Concentration |
|---|---|---|---|
| Basal Media | DMEM/F-12 1:1 mixture | Insulin | 5 ug/ml |
| FBS | 10% (v/v) | Ascorbic acid | 0.2 mM |
| EGF | 20 ng/ml | Antibiotic-antimycotic | 1 X |

After 3 days of culture, the adult stem cells derived from the cultured amniotic epithelial cells were washed with HBSS buffer, and then incubated with Tryple-express (Gibco) or 0.25% trypsin-EDTA at 37° C. for 10 minutes. An FBS-containing medium was added thereto to inactivate trypsin, and then $5\times10^6$ stem cells derived from the amniotic epithelial cells were obtained and seeded into a fresh medium and subcultured. For each reseeding for subcultures, 10 µM of ROCK inhibitor was added to each fresh medium.

Figure 2:
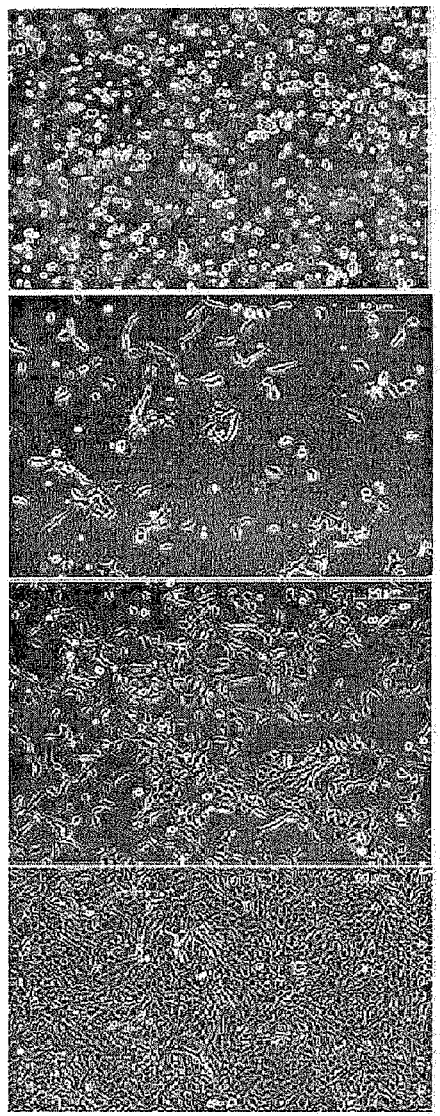
FIG. 2 is photographs showing enhanced ability of amniotic epithelial cell-derived adult stem cells cultured in the presence of a ROCK inhibitor.

The results of the culture of the amniotic epithelial stem cell-derived adult stem cells carried out according to the above procedure are shown in FIG. 2. As can be seen in FIG. 2, before the addition of the ROCK inhibitor, the number of the adult stem cells was decreased, but when the ROCK inhibitor was added 4 days after the isolation of the amniotic epithelial cells, and then cultured, the number of the adult stem cells was rapidly increased.

2-2: Comparison of the Abilities of Stem Cells to Proliferate at Various Concentrations of ROCK Inhibitor In order to examine the proliferation potential of amniotic epithelial cell-derived adult stem cells at various concentrations of ROCK inhibitor, the amniotic epithelial cells obtained in Example 1 were subcultured in DMEM/F-12 media containing FBS, ascorbic acid, epidermal growth factor, insulin and an antibiotic, to which ROCK inhibitor Y-27632 has been added at various concentrations of 100 µM, 1 µM, 100 nM and 10 nM. After 1 day and 4 days of the subculture, the optimum ROCK inhibitor Y-27632 concentration for the culture of the adult stem cells was examined.

Figure 3:
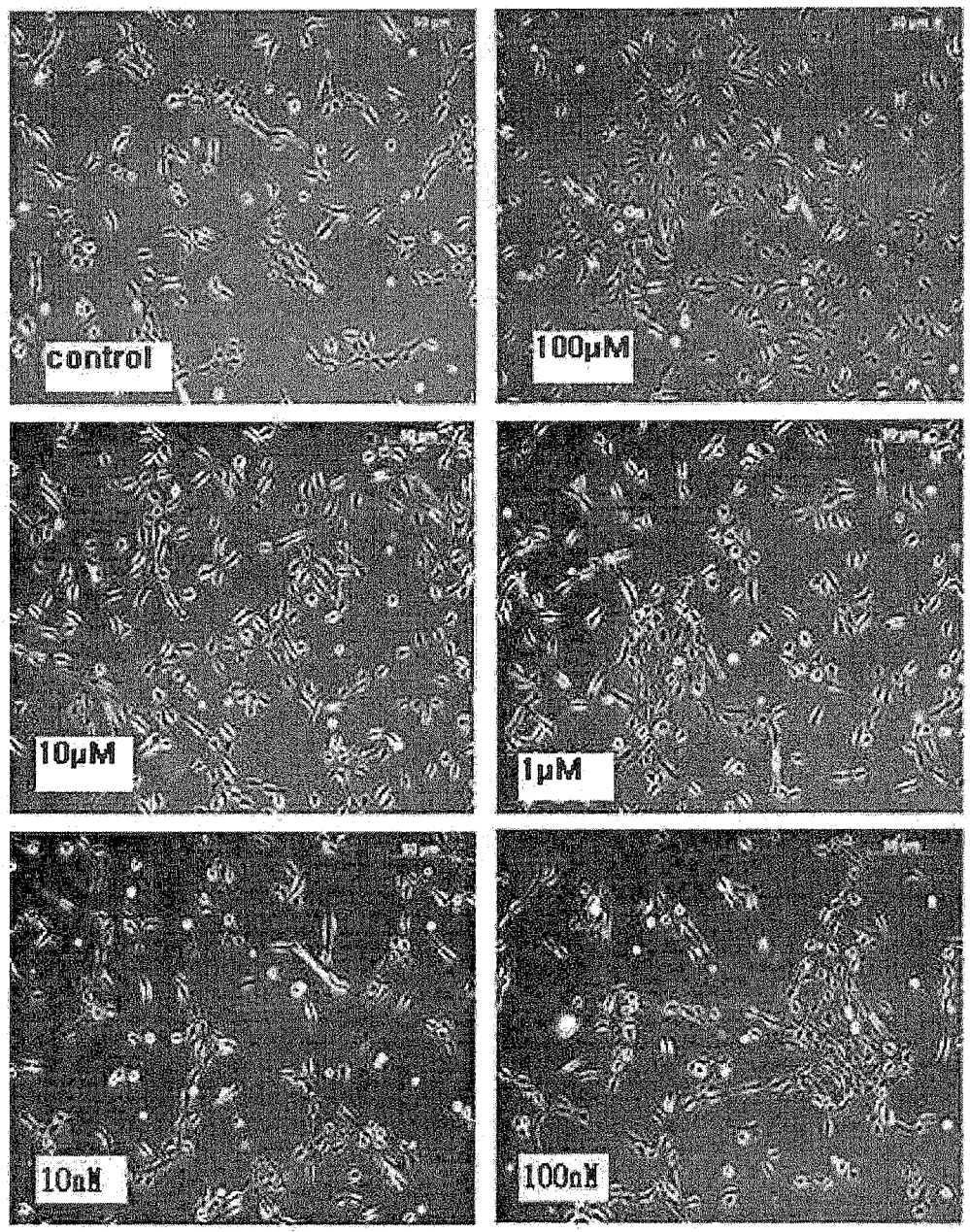
FIG. 3 is photographs showing a comparison of the enhanced ability of adult stem cells to proliferate, 1 day after treatment with the ROCK inhibitor at various concentrations.
Figure 4:
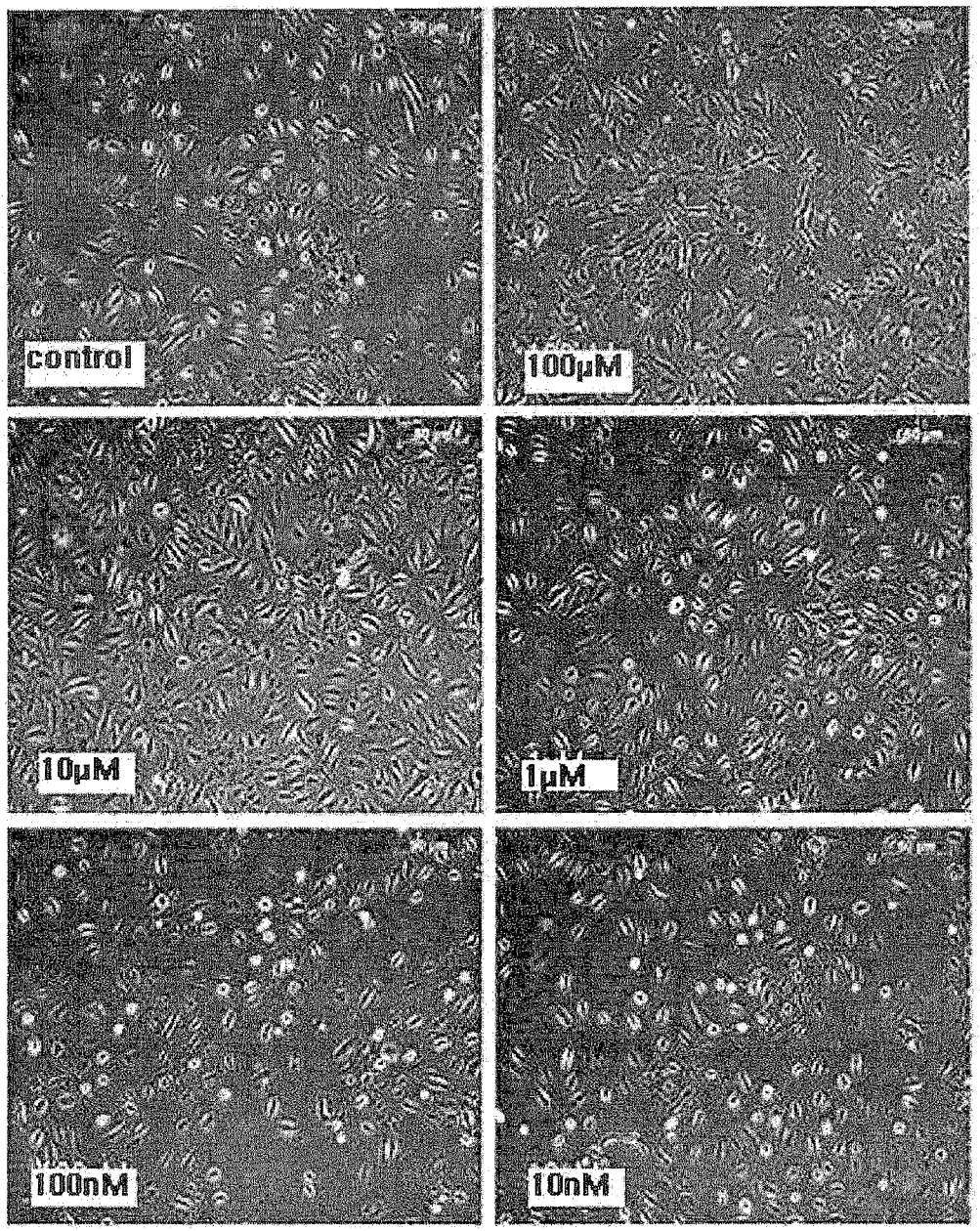
FIG. 4 is photographs showing a comparison of the enhanced ability of adult stem cells to proliferate, 4 days after treatment with the ROCK inhibitor at various concentrations.

As a result, as shown in FIG. 3 and FIG. 4, in the group treated with 10 nM of the ROCK inhibitor, the degree of proliferation did not greatly differ from that in the control not treated with the ROCK inhibitor, and in the group treated with 100 µM of the ROCK inhibitor, the proliferation of the cells was significantly increased, but a cell morphology change or cell differentiation appeared. Thus, it was consirmed that the preferred concentration of the ROCK inhibitor was in the range from 10 nM to 100 µM, and the most preferred concentration was about 10 µM.

Comparative Example 1

Effect of the Addition of ROCK Inhibitor on Promotion of Proliferation of Stem Cells In order to examine the effect of ROCK inhibitor, $4\times10^6$ amniotic epithelial cells obtained in Example 1 were subcultured in a DMEM/F-12 medium containing FBS, ascorbic acid, epidermal growth factor, insulin and an antibiotic for 4 days. Then, the cells were seeded into each of a medium containing 10 µM of the ROCK inhibitor Y-27632 and a medium containing no ROCK inhibitor and were observed 1 day, 2 days and 3 days after seeding.

Figure 5:
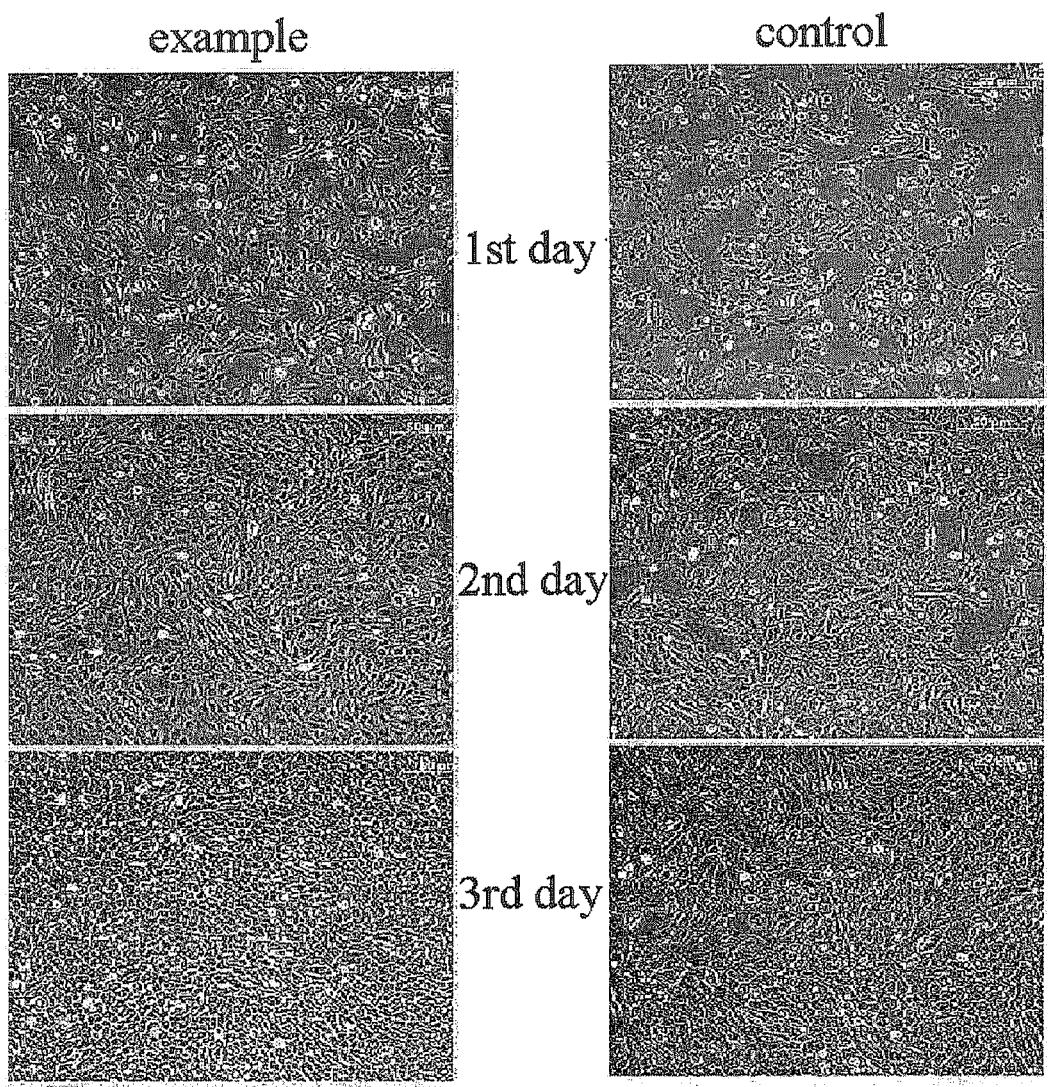
FIG. 5 shows the results obtained by comparing the ability of stem cells to proliferate when cultured with/without the ROCK inhibitor.

As a result, as can be seen in FIG. 5, when the obtained amniotic epithelial cells were cultured in the absence of the ROCK inhibitor, the proliferation of adult stem cells was very slow due to apoptosis. However, when the amniotic epithelial cells were cultured in the presence of the ROCK inhibitor, apoptosis of the amniotic epithelial cells was inhibited, while the proliferation of adult stem cells was significantly increased.

Trypsin treatment which has been conventionally used in subculture has a problem in that the efficiency of culture is reduced due to the toxicity of trypsin, but it could be seen that the addition of the ROCK inhibitor activated the proliferation of adult stem cells by preventing apoptosis caused by trypsin treatment and inhibiting cell differentiation, while it assisted in the stable proliferation of undifferentiated adult stem cells.

Example 3

Comparison of the Abilities of Stem Cells to Proliferate according to ROCK Inhibitor Treatment Period In order to further improve the proliferation ability of the amniotic epithelial cells obtained in Example 1, the method used in the embryonic stem cell study (Watanabe et al., *Nature Biotechnology*, 25:681, 2007) and the method of adding ROCK inhibitor during the culture were compared. In other words, the culture in which 10 µM of ROCK inhibitor was added only before reseeding was compared with the culture in which the ROCK inhibitor was added even after reseeding.

Figure 6:
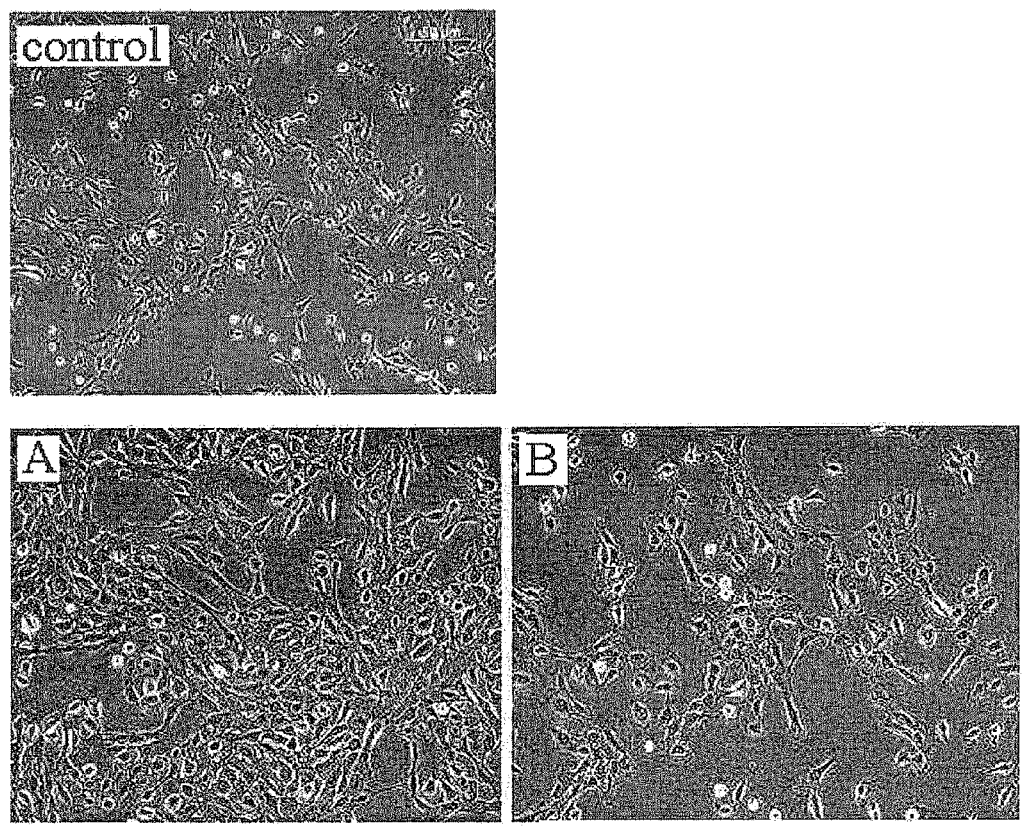
FIG. 6 is photographs showing the results obtained by comparing the ability of amniotic epithelial cell-derived adult stem cells to proliferate according to the ROCK inhibitor treatment period (Control: cells cultured for 1 day without treatment with the ROCK inhibitor; A: cells treated with the ROCK inhibitor only before reseeding and cultured for 1 day, and B: cells treated with the ROCK inhibitor even after reseeding and cultured for 1 day).

As a result, as can be seen in FIG. 6, in the case (A) of treatment with the ROCK inhibitor only before reseeding, the proliferation ability of the adult stem cells derived from the amniotic epithelial cells was clearly increased compared to the control without ROCK inhibitor treatment. Meanwhile, in the case (B) in which the ROCK inhibitor was continuously added during the reseeding and culture procedure, the proliferation ability of adult stem cells was superior compared to the case (A) in which the ROCK inhibitor was added only before reseeding. In other words, in the case (B) in which the ROCK inhibitor was continuously added even during the culture after reseeding, the proliferation ability of the amniotic epithelial cell-derived adult stem cells was most significantly increased.

Example 4

Increase in Stem Cell Proliferation Ability according to Replacement of Medium during Culture of Amniotic Epithelial Cells The amniotic epithelial cells obtained in Example 1 were cultured in each of DMEM medium and K-SFM medium for 3 days, 6 days and 8 days, respectively.

The DMEM medium was supplemented with FBS, epidermal growth factor, ascorbic acid, nonessential amino acids and an antibiotic, and the K-SFM medium was supplemented with FBS, epidermal growth factor, ascorbic acid, hydrocortisone, NAC, insulin and an antibiotic. As a result, as shown in FIG. 7, it was observed that the proliferation ability of the amniotic epidermal cell-derived adult stem cells was higher in the DMEM medium than in the K-SFM medium.

Meanwhile, diversified experiments were performed for the mass production of amniotic epithelial cell-derived adult stem cells. As a result, as can be seen in FIG. 8, the method of replacing the DMEM medium with the K-SFM medium in the primary subculture increased the proliferation of adult stem cells derived from amniotic epithelial cells. In addition, when the adult stem cells were cultured in the DMEM medium for 4 days and observed, the stem cells proliferated at almost similar rate. Moreover, when the DMEM medium was replaced with the K-SFM medium after 4 days of the primary subculture, and the cells were cultured in the replaced medium for 2 days, the adult stem cells cultured in the replaced K-SFM medium showed higher proliferation ability compared to the adult stem cells cultured in the DMEM medium alone without replacement of the medium.

Example 5

Characteristics of Adult Stem Cells Derived from Amniotic Epithelial Cells 5-1: Flow Cytometry Analysis of Surface Antigen Expression The amniotic epithelial cell-derived adult stem cells cultured in Example 2 were characterized by surface CD series antigen markers. CD9 (epithelial cell, adhesion), CD29 (mononuclear cell marker), CD31 (endothelial cell and stem cell marker), CD34 (hematopoietic stem cell marker), CD45 (PTPR, ASV, Leukocyte marker), CD49f (integrin alpha 6 marker), CD73, CD90 (mononuclear stem cell marker), CD105 (TGF beta 1 marker) and CD133 (hematopoietic stem marker) were applied for FACS analysis.

The amniotic epithelial cell-derived adult stem cells obtained in Example 2 were washed with PBS and treated with trypsin. Then, the cells were collected and centrifuged at 1500 rpm for 5 minutes. After the supernatant was discarded, the cells were added to a blocking buffer solution (5% serum (normal goat serum+normal horse serum) and incubated at 4° C. for 60 minutes, followed by centrifugation at 1500 rpm for 5 minutes. After the supernatant was discarded, the cells were suspended in PBS and dispensed into each well at a cell density of $1\times10^5$ cells which is the same number of a negative control and CD antigen markers. An R-phycoerythrin (PE)/FITC (fluorescein isothiocyanate)-conjugated mouse anti-human monoclonal antibody was added to each well, and the cells were incubated at 4° C. for 40 minutes. After incubation, the cells were centrifuged at 1500 rpm for 3 minutes. After the supernatant was removed, the cells were washed with PBS and centrifuged at 1500 rpm for 3 minutes. Then, after the supernatant was removed, the cells were washed with PBS and centrifuged at 1500 rpm for 3 minutes. After the supernatant was removed, the cells were analyzed using a flow cytometer.

The cells were stained with FITC (fluorescein isothiocyanate)-conjugated anti-human CD9 (Becton-Dickinson), CD34 (Becton-Dickinson), CD45 (Becton-Dickinson), CD105 (Becton-Dickinson) and PE (phycoerythrin)-conjugated anti-human CD29 (Becton-Dickinson), CD31 (Becton-Dickinson), CD49f (Becton-Dickinson), CD73 (Becton-Dickinson), CD90 (Becton-Dickinson) and CD133 (Miltenyi biotec). A replicate sample was used as an unstained control to ensure specificity.

As a result, as shown in FIGS. 9 and 10, with respect to immunological characteristics, the amniotic epithelial cell-derived adult stem cells were positive for CD9, CD29, CD49f, CD73, CD90 and CD105, and were negative for CD31, CD34, CD45 and CD133.

5-2: Sternness of Adult Stem Cells Derived from Amniotic Epithelial Cells

The amniotic epithelial cell-derived adult stem cells obtained in Example 2 were washed three times with PBS and fixed with 4% paraformaldehyde-containing PBS at room temperature for 30 minutes. After the cells were washed three times with PBS for 3 minutes each time, the cells were subjected to permeabilization with 0.1% Triton-X100-containing PBS at room temperature for 10 minutes. After the cells were washed three times with PBS for 3 minutes each time, the cells were incubated with blocking buffer (2.5% serum solution, NSG+NHS) at room temperature for 30 minutes and incubated with primary antibody-containing PBS at room temperature for 1 hour. The cells were washed three times with PBS for 5 minutes each time and incubated with a secondary antibody at room temperature for 30 minutes in dark conditions. The cells were washed three times with PBS, and then mounted. The cells thus obtained were examined for specificity of SSEA 4, Oct-4, Tra-1-60, Tra-1-81, Cytokeratin and E-cadherin.

As a result, as shown in FIG. 11, the adult stem cells according to the present invention were positive for SSEA 4, Oct-4, Tra-1-60 and Tra-1-81, which can be considered to be undifferentiated cell markers, that is, stem cell markers. Also, the adult stem cells were positive for Cytokeratin and E-cadherin, which can be considered to be epithelial cell markers.

5-3: Morphological Characteristics of Adult Stem Cells Derived from Amniotic Epithelial Cells The amniotic epithelial cell-derived adult stem cells obtained in Example 2 were taken out of the incubator and observed under a Zeiss Axiovert 200 fluorescence microscope at 100× magnification. Also, the cells were photographed with an AxioCam MRm CCD mounted on the microscope. The diameter of the cells was measured using provided AxioVision ver. 4.5 program, and the size and nucleus of the cells and the size of the cytoplasm were examined from the photograph, thus determining the morphology of the amniotic epithelial cell-derived stem cells.

As a result, as shown in FIG. 12, the adult stem cells according to the present invention maintained the typical morphology of rectangular parallelepiped- or dice-shaped, slightly rounded epithelial cells, and the size (diameter) of the cells during the culture was about 5-10 μm.

Example 6

Figure 13:
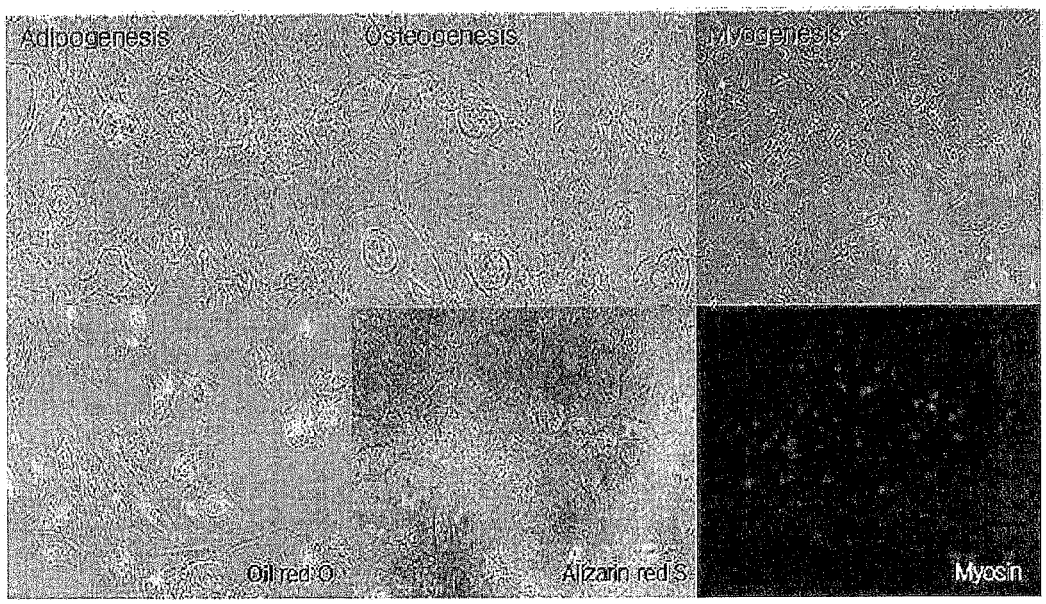
FIG. 13 is photographs showing the adipogenesis, osteogenesis and myogenesis of amniotic epithelial cell-derived adult stem cells.

Differentiation of Adult Stem Cells Derived from Amniotic Epithelial Cells 6-1: Differentiation into Adipocytes The amniotic epithelial cell-derived adult stem cells obtained in Example 2 were cultured in adipogenesis induction medium (Nonhematopoietic AdipoDiff Medium; Miltenyi Biotec) for 3 weeks (37° C.; 5% $CO_2$; medium replacement cycle: 3-4 days) to induce the differentiation of pluripotent stem cells into adipocytes. 21 days (3 weeks) after the start of the culture, the cells were analyzed using the Oil red 0 staining method. As a result, it could be observed that the amniotic epithelial cell-derived adult stem cells according to the present invention differentiated into adipocytes (FIG. 13).

6-2: Differentiation into Osteogenic Cells

The amniotic epithelial cell-derived adult stem cells obtained in Example 2 were cultured in osteogenesis induction medium (nonhematopoietic osteoDiff medium, Miltenyi Biotec) for 2 weeks (37° C.; 5% $CO_2$; medium replacement cycle: 3-4 days) to induce the differentiation of pluripotent stem cells into osteogenic cells. 14 days (2 weeks) after the start of the culture, the cells were analyzed using the Alizalin red S staining method. As a result, it was observed that the amniotic epithelial cell-derived adult stem cells differentiated into osteogenic cells (FIG. 13).

6-3 Differentiation into Myocytes

The amniotic epithelial cell-derived adult stem cells obtained in Example 2 were cultured in myogenic induction medium (Skeletal Muscle Cell Medium, LONZA) for 3 weeks (37° C.; 5% $CO_2$; medium replacement cycle: 3-4 days). 21 days (3 weeks) after the start of the culture, the cells were immunostained.

As a result, the amniotic epithelial cell-derived adult stem cells according to the present invention showed positive staining for myosin that is a skeletal muscle cell-specific antigen. This suggests that the amniotic epithelial cell-derived adult stem cells according to the present invention differentiated into myocytes (FIG. 13).

6-4: Differentiation into Neurocytes

The amniotic epithelial cell-derived adult stem cells obtained in Example 2 were cultured in neurogenic induction medium (Neural Progenitor Media Systems, LONZA) for 2 weeks (37° C.; 5% $CO_2$; medium replacement cycle: 3-4 days) to induce differentiation into neurocytes. 14 days (2 weeks) after the start of the culture, the cells were immunostained.

Figure 14:
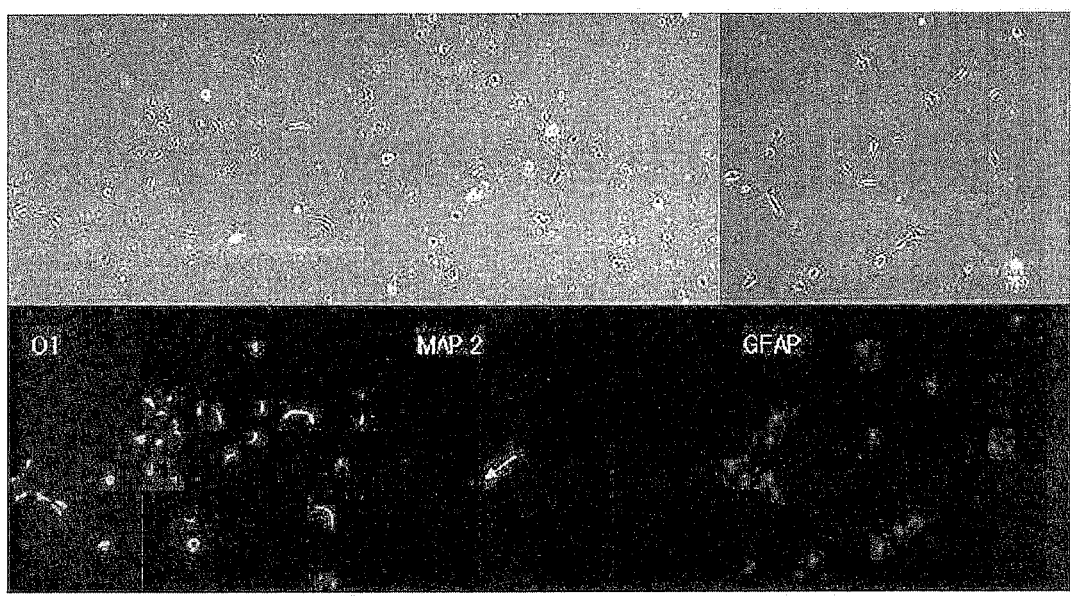
FIG. 14 is a photograph showing the neurogenesis of amniotic epithelial cell-derived adult stem cells.

As a result, as shown in FIG. 14, the amniotic epithelial cell-derived adult stem cells according to the present invention showed positive staining for GFAP (glial fibrillary acidic protein), O1 (oligodendrocyte marker) and MAP2 (microtubule associated protein) which are antigens specific for astrocytes in the nervous system. This suggests that the amniotic epithelial cell-derived adult stem cells according to the present invention differentiated into neurocytes.

Example 7

Evaluation of would Healing Effect

The amniotic epithelial cell-derived adult stem cells were administered to an athymic nude mouse wound model by the intradermal route, and then the wound healing ability thereof was compared with a saline control group.

As the test animals, 4-5-week-old Bald/c-nu Slc athymic nude mice (Central Laboratory Animals Inc., Korea) were used and allocated to 2 groups as shown in Table 3 below.

TABLE 3

| Group | Dosage | Volume (μl) | No. of animals | Route of administration |
|---|---|---|---|---|
| Control | 0 | 50 (saline) | 6 | intra dermis |
| AEpSC | $2 \times 10^5$ cells | 50 (saline) | 3 | intra dermis |

After the animals were allocated to 2 groups as shown in Table 3, individual identification cards were attached to breeding cages, and each animal was separately bred in each breeding cage in order to identify each individual animal. As a test material, each of 50 μl of saline and 50 μl of $2 \times 10^5$ cells AEpSC was prepared in a 29 G insulin syringe in a clean bench 30 minutes before the start of the test.

1 hour before surgery, the weight of each test animal was measured, administered with an antibiotic and anesthetized. Then, the central portion of the back of each test animal was disinfected with alcohol cotton, and a full-thickness wound was induced at the central back portion using a 5 mm-diameter biopsy punch. Immediately after induction of the wound, a total of 50 μl of the prepared test material was injected into three intradermal sites near the wound. The locations of injection were spaced about 1 cm apart from the periphery of the wound in order to minimize the loss of the test material through the wound surface.

Figure 15:
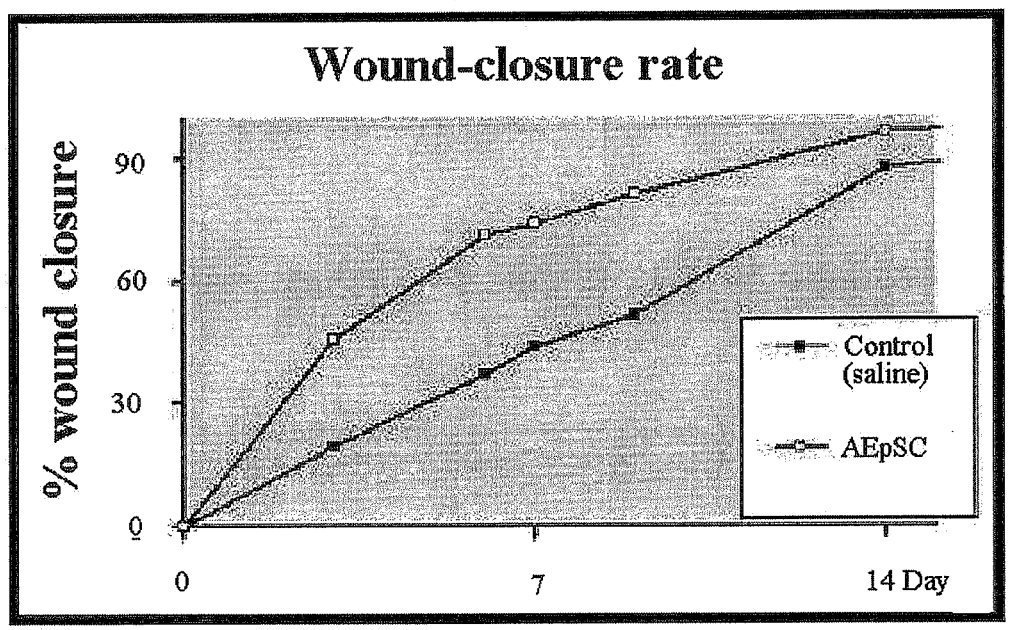
FIG. 15 is a graphic diagram showing the results obtained by observation of wound closure rates in an animal wound model.

To examine the wound healing effect, the condition of the animals was examined once or more everyday, and the wound portion was photographed immediately, 3 days, 6 days, 7 days, 9 days and 14 days after surgery. The analysis results are shown in FIG. 15. FIG. 15 was obtained by placing circular filter paper of the same size as that of the wound on the wound, photographing the wound together with the circular filter paper as the reference pixel area.

As a result, as shown in FIG. 15, it could be observed that the wound closure rate of the group administered with the amniotic epithelial cell-derived stem cells was higher than that of the group administered with saline.

Figure 16:
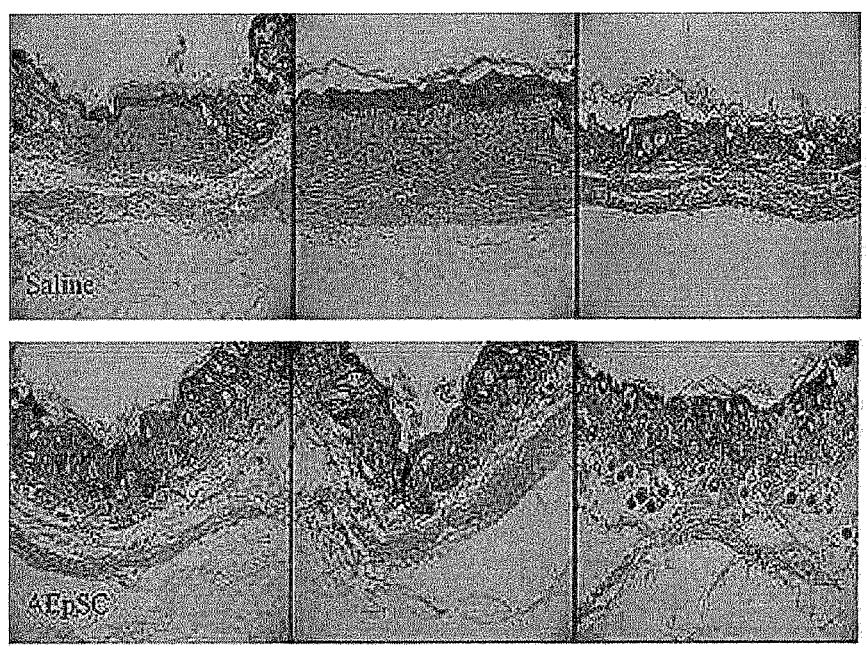
FIG. 16 is H&E staining photographs of recovered wound skin tissue in a group administered with amniotic epithelial cell-derived adult stem cells.

In addition, 21 days after surgery at which the induced wound was completely recovered, the test animals were autopsied and subjected to a skin biopsy. The results of tissue biopsy in each group after the induced wound was recovered, are shown in FIG. 16. As shown in FIG. 16, in the skin of the control, there was only fibrous tissue mass, whereas, in the group administered with the amniotic epithelial stem cells, a large amount of skin appendages such as hair follicles and sweat glands were observed in the recovered skin tissue.

From such results, it could be found that the amniotic epithelial stem cells according to the present invention functioned to promote the reepithelialization of skin tissue and facilitate the regeneration of skin appendages.

INDUSTRIAL APPLICABILITY

As described above in detail, the human amniotic epithelial cell-derived stem cells according to the present invention are easily extracted compared to existing therapeutic stem cells such as umbilical cord blood stem cells and bone marrow stem cells, the initial yield thereof is increased through DTT treatment, and the proliferation rate thereof is significantly increased by culturing them in a ROCK inhibitor-containing medium. Thus, the method of the present invention can be used to efficiently prepare adult stem cells useful as cell therapeutic agents.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for preparing adult stem cells derived from human amniotic epithelial cells, the method comprising the steps of:
    treating human amniotic tissue with dithiothreitol (DTT);
    treating the DTT-treated human amniotic tissue with 0.025-0.125% trypsin, thereby yielding a suspension;
    isolating human amniotic epithelial cells from the suspension;
    culturing said human amniotic epithelial cells in a medium containing the Rho-associated kinase (ROCK) inhibitor Y-27632; and
    collecting stem cells from the medium.

2. A method for proliferating and maintaining adult stem cells derived from human amniotic epithelial cells, the method comprising the steps of:
  treating human amniotic tissue with dithiothreitol (DTT);
  treating the DTT-treated human amniotic tissue with 0.025-0.125% trypsin, thereby yielding a suspension;
  isolating human amniotic epithelial cells from the suspension;
  culturing said human amniotic epithelial cells in a medium containing the Rho-associated kinase (ROCK) inhibitor Y-27632;
  collecting human amniotic epithelial cell-derived stem cells from the medium; and
  subculturing said human amniotic epithelial cell-derived stem cells in a medium containing the Rho-associated kinase (ROCK) inhibitor Y-27632.

3. The method according to claim 1 or 2, wherein the concentration of the ROCK inhibitor Y-27632 is 10 nM to 100 µM.

4. The method according to claim 1 or 2, wherein said medium is DMEM (Dulbecco's modified eagle medium) or K-SFM (keratinocyte serum free medium).

5. The method according to claim 2, wherein the medium in the subculturing step is DMEM, and
  further comprising a step of replacing the DMEM with K-SFM.

6. The method according to claim 1 or 2, wherein said medium is a mixed medium consisting of a 1:1 mixture of DMEM and F-12.

7. The method according to claim 6, wherein the medium additionally contains ascorbic acid, epidermal growth factor (EGF), insulin, antibiotics and FBS (fetal bovine serum).

8. The method according to claim 2, wherein the ROCK inhibitor Y-27632 is added at the start of the subculturing step.

* * * * *